United States Patent [19]

Hoffmann et al.

[11] Patent Number: 4,609,646
[45] Date of Patent: * Sep. 2, 1986

[54] 2-(THI)OXO-1,3,2-OXAZAPHOSPHOLANES AS SYNERGIZING AGENTS FOR PESTICIDES

[75] Inventors: Hellmut Hoffmann; Bernd-Wieland Krüger, both of Wuppertal; Wolfgang Behrenz, Overath, all of Fed. Rep. of Germany

[73] Assignee: Bayer Aktiengesellschaft, Leverkusen, Fed. Rep. of Germany

[*] Notice: The portion of the term of this patent subsequent to Sep. 25, 2001 has been disclaimed.

[21] Appl. No.: 581,470

[22] Filed: Feb. 17, 1984

Related U.S. Application Data

[62] Division of Ser. No. 401,461, Jul. 26, 1982, Pat. No. 4,473,558, which is a division of Ser. No. 202,906, Nov. 3, 1980, Pat. No. 4,387,060.

[30] Foreign Application Priority Data

Nov. 8, 1979 [DE] Fed. Rep. of Germany ....... 2945036
Nov. 8, 1979 [DE] Fed. Rep. of Germany ....... 2945101

[51] Int. Cl.$^4$ .................... A01N 57/36; C07F 9/24
[52] U.S. Cl. ...................................... 514/77; 514/110; 558/81
[58] Field of Search .................. 260/936; 514/110, 77

[56] References Cited

U.S. PATENT DOCUMENTS

| | | | |
|---|---|---|---|
| 2,865,948 | 12/1958 | Fusco | 260/936 |
| 3,285,999 | 11/1966 | Buchner et al. | 260/936 |
| 4,190,651 | 2/1980 | Eto et al. | 260/936 |
| 4,473,558 | 9/1984 | Hoffmann et al. | 424/186 |

FOREIGN PATENT DOCUMENTS 2810923  9/1978  Fed. Rep. of Germany.

OTHER PUBLICATIONS

Article Entitled "Synthesis and Insecticidal Activities of Five-Membered Cyclic Phosphoramidates and Phosphoramidothiolates" by Shinkichi Tawata et al, J. Pesticide Sci. 3, 257–266 (1978).
Chemical Abstracts, vol. 91, 1979, p. 216.
Chemical Abstracts vol. 90, 1979 p. 164.
C. R. Acad. Sc. Paris, t. 289 (o juillet 1979), Serie C-61.
C. A. vol. 90, 1979, pp. 163–164.
Deuillers et al., "C. R. Acad. Sc. Paris", C. vol. 267, (1968), pp. 849–852.

*Primary Examiner*—Anton H. Sutto
*Attorney, Agent, or Firm*—Sprung, Horn, Kramer & Woods

[57] ABSTRACT

In a synergistic pesticidal composition comprising (1) a pesticidally active compound and (2) a synergizing agent in amount sufficient to synergize the pesticidal activity of the pesticidally active compound, the improvement which comprises employing as the syngerizing agent a 2-(thi)oxo-1,3,2-oxazaphospholane of the formula

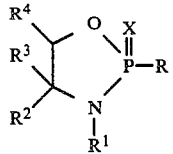

in which
X represents oxygen or sulphur,
R represents an optionally substituted alkyl, alkenyl, alkynyl, phenyl, alkoxy, alkenoxy, alkynoxy, alkylthio, aralkoxy, amino, mono- or di-alkylamino, heterocyclic amino, N-alky-N-aryl-amino, phenoxy or phenylthio radical,
$R^1$ represents hydrogen, optionally subsituted alkyl, aralkyl, alkenyl, alkynyl or dialkylaminoalkyl,
$R^2$ represents hydrogen, alkylthioalkyl; or optionally substituted alkyl or aralkyl, or $R^1$ and $R^2$ together represent alkylene,
$R^3$ represents hydrogen or alkyl and
$R^4$ represents hydrogen, alkyl, or phenyl.

5 Claims, No Drawings

2-(THI)OXO-1,3,2-OXAZAPHOSPHOLANES AS SYNERGIZING AGENTS FOR PESTICIDES

This is a division of application Ser. No. 401,461, filed July 26, 1982, now U.S. Pat. No. 4,473,558, which is a division of application Ser. No. 202,906, filed Nov. 3, 1980, now U.S. Pat. No. 4,387,060.

The invention relates to a new pesticidal, in particular insecticidal and acaricidal, synergistic combinations of certain 2-(thi)oxo-1,3,2-oxazaphospholanes, some of which are new, and pesticidal, in particular insecticidal and acaricidal, active compounds.

It is already known that the following active compounds and groups of active compounds have pesticidal properties, in particular insecticidal and acaricidal properties:

(A) carbamic acid esters, such as N-methyl-carbamic acid O-(2-iso-propoxyphenyl)ester, N-methyl-carbamic acid O-(2,3-dihydro-2,2-dimethyl-7-benzofuranyl)ester, N-methyl-carbamic acid O-(2,3-dimethyl-methylenedioxy)phenyl)ester and N-methyl-carbamic acid O-(1-methylthioethylidene-amino)ester;

(B) carboxylic acid esters, such as 2,2-dimethyl-3-(2-methyl-propen-1-yl)-cyclopropane-carboxylic acid 2,3,4,5-tetrahydro-phthalimido-methyl ester, 2,2-dimethyl-3-(2,2-dibromo-vinyl)-cyclopropane-carboxylic acid α-cyano-3-phenoxy-benzyl ester, 2,2-dimethyl-3-(2,2-dichlorovinyl)-cyclopropanecarboxylic acid pentafluoro-benzyl ester and acetic acid (2,2,2-trichloro-1-(3,4-dichlorophenyl)ethyl)ester, and the naturally occurring pyrethrins;

(C) phosphoric acid esters and phosphonic acid esters, such as O,O-dimethyl O-(2,2-dichloro-vinyl)phosphate; and (D) halogeno(cyclo)alkanes, such as hexachlorocyclohexane.

Synergistic mixtures of carbamic acid esters, for example 2-isopropoxy-phenyl N-methylcarbamate, or of phosphoric acid esters, for example O,O-diethyl O-(2-isopropyl-4-methyl-pyridmidin-6-yl)thionophosphate, or of naturally occurring or synthetic pyrethroids and piperonyl ethers, for example α-(2-(2-butoxy-ethoxy)-ethoxy)-4,5-methylenedioxy-2-propyl-toluene, are also known (see Bull. Wld. Health Org. 1966, 35, pages 691–708; Schrader, G., Die Entwicklung neuer insektizider Phosphorsäureester (The development of new insecticidal phosphoric acid esters) 1963, page 158; and Perkov, W., Die Insektizide (Insecticides), 1966, pages 516–524). However, the activity of these synergistic active compound combinations is not satisfactory. Only α-(2-(2-butoxy-ethoxy)-ethoxy)-4,5-methylenedioxy-2-propyl-toluene has hitherto achieved a certain importance in practice.

The present invention now provides a pesticidal composition containing as active ingredients (1) a 2-(thi)oxo-1,3,2-oxazaphospholane of the general formula

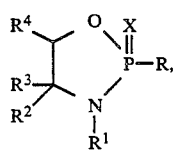

(I)

in which
X represents oxygen or sulphur,
R represents an optionally substituted alkyl, alkenyl, alkynyl, phenyl, alkoxy, alkenoxy, alkynoxy, alkylthio, aralkoxy, amino, mono- or di-alkylamino, heterocyclic amino, N-alkyl-N-aryl-amino, phenoxy or phenylthio radical,
$R^1$ represents hydrogen, optionally substituted alkyl, aralkyl, alkenyl, alkynyl or dialkylaminoalkyl,
$R^2$ represents hydrogen, alkylthioalkyl, or optionally substituted alkyl, or aralkyl, or $R^1$ and $R^2$ together represent alkylene,
$R^3$ represents hydrogen or alkyl and
$R^4$ represents hydrogen, alkyl, or phenyl,
and (2) a pesticidally active compound, in particular an insecticidally or acaricidally active compound, alone or in admixture with a solid or liquid or liquefied gaseous diluent or carrier.

These compositions have an especially high pesticidal action, in particular an especially high insecticidal and acaricidal action.

The pesticidal component (2) is preferably selected from (A) carbamic acid esters (B) carboxylic acid esters, including the naturally occurring or synthetic pyrethroids, (C) phosphoric acid esters and phosphonic acid esters, and (D) halogeno(cyclo)alkanes; of course, component (2) can be a mixture of two or more of these compounds.

The ratio of component (1) to component (2) is advantageously about 0.1:10 to 10:0.1, preferably about 1:5 to 5:1, by weight.

The active compounds with which the compounds of the formula (I) exhibit a particularly good synergistic action are discussed below.

Preferred carbamic acid esters (A) are those of the general formula

(II)

in which
$R^5$ represents hydrogen or $C_1$–$C_4$-alkyl,
$R^6$ represents $C_1$–$C_4$-alkyl, $C_1$–$C_4$-alkylcarbonyl which is optionally substituted by halogen, by hydroxy or by methylthio, or the radical S–Z, wherein
Z represents optionally halogen-substituted $C_1$–$C_4$-alkyl, phenyl which optionally carries one or more substituents selected from halogen, cyano, $C_1$–$C_4$-alkyl, trihalogenomethylthio, trihalogenomethyl and nitro, or $C_1$–$C_4$-alkoxy-carbonyl and
$R^7$ represents an optionally substituted aryl, heterocyclic or oxime radical. Carbamic acid esters of the formula (II) in which
$R^7$ represents a phenyl, naphthyl, 2,3-dihydrobenzofuranyl, methylenedioxyphenyl, dioxolanylphenyl, pyrazolyl or pyrimidinyl radical which optionally carries one or more substituents selected from $C_1$–$C_4$-alkyl, $C_1$–$C_4$-alkoxy, $C_1$–$C_4$-alkoxy-methyl, $C_1$–$C_4$-alkylthio, $C_1$–$C_4$-alkylthio-methyl, $C_1$–$C_4$-alkylamino, di-($C_1$–$C_4$-alkyl)-amino, di-($C_2$–$C_4$-alkenyl)-amino and halogen, or in which
$R^7$ represents an alkylideneamino radical of the general formula

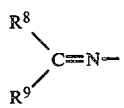 (IIa)

in which

R$^8$ and R$^9$ are identical or different and individually represent C$_1$–C$_5$-alkyl, C$_3$–C$_8$-cycloalkyl, C$_2$–C$_5$-alkenyl, C$_2$–C$_5$-alkynyl, C$_1$–C$_4$-alkoxy, C$_1$–C$_4$-alkylthio, C$_1$–C$_4$-alkylthiomethyl, C$_1$–C$_4$-alkoxycarbonyl, carbamoyl, cyano or phenyl, or R$^8$ and R$^9$ together represent an optionally C$_1$–C$_4$-alkyl-substituted C$_2$–C$_3$-alkylenedioxy or C$_2$–C$_3$-alkylenedimercapto group, are very particularly preferred.

Examples of the carbamic acid esters of the formula (II) which may be mentioned are: 2-methyl-phenyl, 2-ethyl-phenyl, 2-iso-propyl-phenyl, 2-sec.-butyl-phenyl, 2-methoxy-phenyl, 2-ethoxy-phenyl, 2-iso-propoxy-phenyl, 4-methyl-phenyl, 4-ethyl-phenyl, 4-n-propyl-phenyl, 4-methoxy-phenyl, 4-ethoxy-phenyl, 4-n-propoxy-phenyl, 3,4,5-trimethyl-phenyl, 3,5-dimethyl-4-methylthio-phenyl, 3-methyl-4-dimethylamino-phenyl, 2-ethylthiomethyl-phenyl, 1-naphthyl, 2,3-dihydro-2,2-dimethyl-7-benzofuranyl, 2,3-(dimethyl-methylenedioxy)-phenyl, 2-(4,5-dimethyl-1,3-dioxolan-2-yl)-phenyl, 1-methylthio-ethylideneamino, 2-methylthio-2-methyl-propylidene-amino, 1-(2-cyanoethylthio)-ethylideneamino and 1-methylthiomethyl-2,2-dimethyl-propylideneamino N-methyl-carbamate.

Preferred carboxylic acid esters (B) are those of the general formula

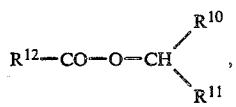 (III)

in which

R$^{12}$ represents an open-chain or cyclic alkyl radical which is optionally substituted by halogen, by alkyl, by cycloalkyl, by alkenyl which is optionally substituted by halogen and/or alkoxy, by phenyl or styryl, in either case optionally substituted by halogen or one or more substituents selected from optionally halogen-substituted alkyl, alkoxy, alkylenedioxy and alkylthio radicals, or by cycloalk(en)yl which is linked in a spirocyclic-like manner and is optionally halogen-substituted and optionally benzo-fused, R$^{10}$ represents hydrogen, alkyl, halogenoalkyl, alkenyl, alkynyl or cyano and R$^{11}$ represents an optionally substituted aryl radical or a heterocyclic radical, or R$^{1C}$ and R$^{11}$, together with the carbon atom to which the two radicals are bonded, form a cyclopentenone ring.

Carboxylic acid esters of the formula (III) in which R$^{12}$ represents the radical

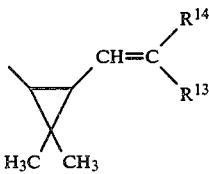

wherein

R$^{14}$ represents hydrogen, methyl, fluorine, chlorine or bromine and

R$^{13}$ represents methyl, fluorine, chlorine, bromine, C$_1$–C$_2$-fluoroalkyl or C$_1$–C$_2$-chlorofluoroalkyl, or phenyl which is optionally substituted by halogen and/or one or more substituents selected from optionally halogen-substituted C$_1$–C$_4$-alkyl, C$_1$–C$_4$-alkoxy, C$_1$–C$_4$-alkylthio and C$_1$–C$_2$-alkylenedioxy radicals, or R$^{13}$ and R$^{14}$ together represent C$_2$–C$_5$-alkanediyl(alkylene), or in which R$^{12}$ represents the radical

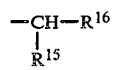

wherein

R$^{16}$ represents phenyl which is optionally substituted by halogen and/or by one or more substituents selected from optionally halogen-substituted C$_1$–C$_4$-alkyl, C$_1$–C$_4$-alkoxy, C$_1$–C$_4$-alkylthio and C$_1$–C$_2$-alkylenedioxy radicals and R$^{15}$ represents isopropyl or cyclopropyl, or in which R$^{12}$ represents methyl or one of the radicals

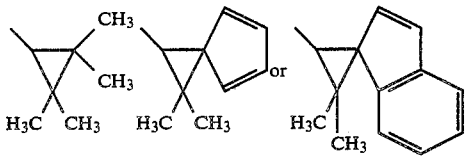

and in which

R$^{10}$ represents hydrogen, C$_1$–C$_4$-alkyl, C$_1$–C$_4$-halogenoalkyl, cyano or ethynyl and R$^{11}$ represents a phenyl, furyl or tetrahydrophthalimido radical which is optionally substituted by halogen and/or by one or more substituents selected from optionally halogen-substituted C$_1$–C$_4$-alkyl, C$_2$–C$_4$-alkenyl, C$_1$–C$_4$-alkoxy, C$_2$–C$_4$-alkenoxy, C$_1$–C$_4$-alkylthio, C$_1$–C$_2$-alkylenedioxy, phenoxy and benzyl radicals, are very particularly preferred.

The naturally occurring pyrethroids are also particularly preferred.

Examples of the carboxylic acid esters of the formula (III) which may be mentioned are: acetic acid [2,2,2-trichloro-1-(3,4-dichlorophenyl)-ethyl]ester, 2,3,4,5-tetrahydrophthalimidomethyl chrysanthemate, 3-phenoxybenzyl[2,2-dimethyl-3-(2,2-dichlorovinyl)-cyclopropane]carboxylate, (5-benzyl-furyl)-methyl 2,2-dimethyl-3-(2-methylpropenyl)-cyclopropane carboxylate, 3-phenoxybenzyl-2,2-dimethyl-3-(2-methylpropenyl)cyclopropane carboxylate, 2,2-dimethyl-3-dichlorovinylcyclopropanecarboxylic acid α-cyano-3'-phenoxy-4'-fluorobenzyl ester, 5-benzyl-3-furylmethyl d-cis(1R,3S,E)-2,2-dimethyl-3-(2-oxo 2,2,4,5-tetrahydrothiophenylidenemethyl)cyclopropane carboxylate, (R,S)-α-cyano-3-phenoxybenzyl (R,S)-2-(4-chlorophenyl)-3-methylbutyrate, (±)-3-allyl-2-methyl-4-oxocyclopent-2-enyl (+)-cis/transchrysanthemate, 2,2-dimethyl-3-dichlorovinyl-cyclopropanecarboxylic acid pentafluorobenzyl ester, [R,S]-α-cyano-3-phenoxybenzyl(1R, 3S)-cis/trans 3-(2,2-dichlorovinyl)-2,2-dimethyl-cyclopropane carboxylate and (S)-α-cyano-m-phenoxybenzyl(1R, 3R)-3-(2,2-dibromovinyl)-2,2-dimethylcyclopropane carboxylate.

Preferred phosphoric acid esters and phosphonic acid esters are those of the general formula

in which

X' represents oxygen or sulphur,

Y' represents oxygen, sulphur, imino or a direct bond between the P atom and $R^{19}$, $R^{17}$ and $R^{18}$ are identical or different and each represents an optionally substituted alkyl or aryl radical and $R^{19}$ represents an optionally substituted alkyl, aryl, heteroaryl, aralkyl or alkenyl radical, an optionally substituted oxime radical, or a radical identical to that to which it is bonded.

Phosphoric acid esters and phosphonic acid esters of the formula (IV) in which $R^{17}$ and $R^{18}$ are identical or different and each represent $C_1$–$C_4$-alkyl or phenyl and $R^{19}$ represents $C_1$–$C_4$-alkyl which is optionally substituted by halogen and/or hydroxyl and/or cyano, phenyl which optionally carries one or more substituents selected from halogen, cyano, nitro, carbamoyl, $C_1$–$C_4$-alkyl-sulphonyl, $C_1$–$C_4$-alkyl-sulphinyl, $C_1$–$C_4$-alkyl-carbonyl, $C_1$–$C_4$-alkyl, $C_1$–$C_4$-alkoxy, $C_1$–$C_4$-alkylthio and $C_1$–$C_4$-alkoxy-carbonyl, $C_2$–$C_4$-alkenyl which is optionally substituted by halogen and/or by halogen-substituted phenyl, $C_1$–$C_4$-alkoxycarbonyl, $C_1$–$C_4$-alkylaminocarbonyl or di-($C_1$–$C_4$-alkyl)-aminocarbonyl, or an oxime radical of the general formula

wherein $R^8$ and $R^9$ have the above-mentioned meanings, but wherein $R^8$ preferably represents cyano and $R^9$ preferably represents $C_1$–$C_4$-alkyl or phenyl, or $R^{19}$ represents a hetero-aromatic radical (such as pyridinyl, quinolinyl, quinoxalinyl, pyrimidinyl, benzo-oxotriazinyl, pyrazolyl or imidazolyl) that optionally carries one or more substituents selected from halogen, $C_1$–$C_4$-alkyl, $C_1$–$C_4$-alkoxy, $C_1$–$C_4$-alkylthio, $C_1$–$C_4$-alkyl-amino, di-($C_1$–$C_4$-alkyl)amino, $C_1$–$C_4$-alkoxymethyl, $C_1$–$C_4$-alkylthiomethyl, $C_1$–$C_4$-alkylsulphinylmethyl and $C_1$–$C_4$-alkyl-sulphonylmethyl, are particularly preferred.

An example of the phosphoric acid esters of the formula (IV) which may be mentioned is O,O-dimethyl O-(2,2-dichloro-vinyl)phosphate.

Preferred halogeno(cyclo)alkanes (D) include, for example, hexachlorocyclohexane, 1,1,1-trichloro-2,2-bis-(4-chlorophenyl)ethane, 1,1,1-trichloro-2,2-bis-(4-methoxyphenyl)-ethane and 1,1-dichloro-2,2-bis-(4-ethylphenyl)-ethane.

Surprisingly, the pesticidal activity of the active compound combinations according to the invention is considerably higher than the action of the individual components or than the sum of the actions of the individual components. It is also considerably higher than the action of active compound combinations with the known synergistic agent piperonyl butoxide.

Formula (I) provides a definition of the synergistic agents to be used in the active compound combinations according to the invention. Preferably, in this formula, X represents oxygen or sulphur, R represents optionally halogen-substituted $C_1$–$C_4$-alkyl, phenyl, $C_1$–$C_5$-alkoxy, $C_1$–$C_4$-alkylthio, amino, $C_1$–$C_4$-alkyl-amino, di-($C_1$–$C_4$-alkyl)-amino, N-phenyl-N-($C_1$–$C_4$-alkyl)-amino, benzyloxy, phenethoxy or phenylthio, or phenoxy which optionally carries one or more substituents selected from halogen, cyano, nitro, carbamoyl, $C_1$–$C_4$-alkylsulphonyl, $C_1$–$C_4$-alkylsulphinyl, $C_1$–$C_4$-alkylcarbonyl, $C_1$–$C_4$-alkyl, $C_1$–$C_4$-alkoxy, $C_1$–$C_4$-alkylthio and $C_1$–$C_4$-alkoxycarbonyl, $R^1$ represents hydrogen, $C_1$–$C_4$-alkyl or 2-di-($C_1$–$C_4$-alkyl)-amino-ethyl, $R^2$ represents hydrogen, $C_1$–$C_4$-alkyl, 2-($C_1$–$C_4$-alkylthio)-ethyl or benzyl, $R^3$ represents hydrogen or $C_1$–$C_3$-alkyl and $R^4$ represents hydrogen or phenyl.

Of course, component (1) in the active compound combinations according to the invention can be two or more compounds of the formula (I).

Compounds of the formula (I) are new and can be prepared by processes which are known from the literature (see, for example, (German Published Specification) DOS No. 2,810,923; Bull. Chem. Soc. Japan 39 (1966), 1296–1297; Bull. Soc. Chim. France 1970, 4341–4347; J. Chem. Soc. Perkin I 1977, 1969; and J. Org. Chem. 31 (1966), 2903–2907).

Compounds of the formula (I) in which R represents an optionally substituted alkoxy, alkenoxy, alkynoxy, alkylthio, amino, heterocyclic amino, alkylamino, dialkylamino, N-alkyl-N-arylamino, phenoxy or phenylthio radical are obtained when 2-(thi)-oxo-2-halogeno-1,3,2-oxazaphospholanes of the general formula

in which

X, $R^1$, $R^2$, $R^3$ and $R^4$ have the above-mentioned meanings and

Hal represents halogen, especially chlorine, are reacted with compounds of the general formula

in which

R represents an optionally substituted alkoxy, alkenoxy, alkynoxy, alkylthio, amino, heterocyclic amino, alkylamino, dialkylamino, N-alkyl-N-arylamino, phenoxy or phenylthio radical, if appropriate in the presence of an acid acceptor, for example sodium methylate or triethylamine, and if appropriate using a diluent, for example ethanol or toluene, at a temperature between 10° and 80° C. Working up is effected by customary methods, for example by extracting the products from the reaction mixture, which has been diluted with water, with toluene, washing the organic phase with water and drying and distilling it.

Compounds of the formula (I) in which

R has the above-mentioned meaning, are also obtained when (thio)phosphonic acid dichlorides, respectively (thio)phosphoric acid dichlorides of the general formula

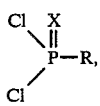
(VII)

in which

X represents oxygen or sulphur and

R has the above-mentioned meaning, (cf. page 2), are reacted with aminoalcohols of the general formula

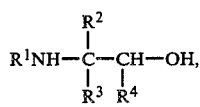
(VIII)

in which $R^1$, $R^2$, $R^3$ and $R^4$ have the above-mentioned meanings, if appropriate in the presence of an acid acceptor, for example triethylamine, and if appropriate using a diluent, for example toluene, at a temperature between 10° and 80° C., and the mixture is worked up as described above.

If, for example, 2-thioxo-2-chloro-5-methyl-1,3,2-oxazaphospholane and methanol are used as starting substances in process variant (a) for the preparation of compounds of the formula (I) and methane-thionophosphonic acid dichloride and 1-amino-propan-2-ol are used as starting substances in process variant (b), the reactions which proceed in the preparative processes can be outlined by the following equations:

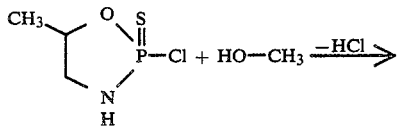
(a)

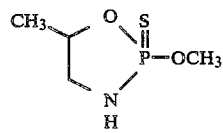

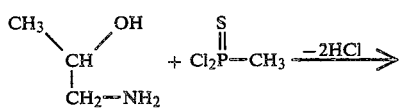
(b)

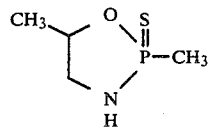

If appropriate, the process variants for the preparation of the compounds according to the invention are carried out also using a suitable solvent or diluent. Possible solvents or diluents are virtually any of the inert organic solvents. These include, as preferences, aliphatic and aromatic, optionally chlorinated hydrocarbons, such as benzene, toluene, xylene, methylene chloride, chloroform and carbon tetrachloride.

Acid acceptors which can be used are any of the customary acid-binding agents. Acid-binding agents which have proved particularly suitable are alkali metal carbonates, such as sodium carbonate and potassium carbonate, alkali metal alcoholates, such as sodium methylate or ethylate and potassium methylate or ethylate, and aliphatic, aromatic or heterocyclic amines, for example triethylamine, dimethylaniline, dimethylbenzylamine and pyridine.

The reaction temperature can be varied within a substantial range. In general, the reaction is carried out between 0° and 100° C., preferably at 10° to 80° C.

The process variants according to the invention are in general carried out under normal pressure.

The starting substances are usually employed in equimolar amounts for carrying out the process variants according to the invention. An excess of one of the reactants provides no substantial advantages. The reaction is in general carried out in a suitable diluent in the presence of an acid acceptor, and the reaction mixture is stirred at the required temperature for several hours. An organic solvent, for example toluene, is then added, if appropriate, and the organic phase is worked up in the customary manner by washing, drying and distilling off the solvent.

For purification of the products, the residue is distilled, if appropriate under reduced pressure.

Those compounds of the formula I are new in which

R represents an optionally substituted alkenyl, alkynyl, phenyl, alkoxy, alkenoxy, alkynoxy, alkylthio, amino, mono- or di-alkylamino, heterocyclic amino, phenoxy or phenylthio radical or, provided that X represents sulphur, optionally substituted alkyl, $R^1$ represents hydrogen or an optionally substituted alkyl, aralkyl, alkenyl or alkynyl radical and $R^2$ represents hydrogen or an optionally substituted alkyl or aralkyl radical, or $R^1$ and $R^2$ together represent alkylene, $R^3$ represents hydrogen, and $R^4$ represents alkyl or, provided that R represents alkenyl, alkynyl, alkenoxy or alkynoxy and/or $R^1$ represents alkenyl or alkynyl or provided that $R^1$ and $R^2$ together represent alkylene, $R^4$ represents hydrogen or phenyl.

Preferably

R represents $C_2$-$C_5$-alkenyl, $C_2$-$C_5$-alkynyl, phenyl, $C_1$-$C_4$-alkoxy, $C_2$-$C_5$-alkenoxy, $C_2$-$C_5$-alkynoxy, $C_1$-$C_4$-alkylthio, amino, $C_1$-$C_4$-alkylamino, di-($C_1$-$C_4$-alkyl)-amino, dimethylaminomethyleneamino, morpholino, pyrrolidino or piperidino, or a phenoxy or phenylthio radical which optionally carries one or more substituents selected from halogen, optionally halogen-substituted $C_1$-$C_4$-alkyl, $C_1$-$C_4$-alkoxy, $C_1$-$C_2$-alkylenedioxy or $C_1$-$C_4$-alkylthio radicals, cyano and nitro, or, provided that X represents sulphur, optionally halogen-substituted $C_1$-$C_4$-alkyl, $R^1$ represents hydrogen, $C_1$-$C_4$-alkyl, di-($C_1$-$C_2$-alkyl)-amino, $C_1$-$C_2$-alkyl or $C_2$-$C_5$-alkenyl and $R^2$ represents hydrogen, $C_1$-$C_4$-alkyl, $C_1$-$C_4$-alkylthio-$C_1$-$C_2$-alkyl or benzyl, or $R^1$ and $R^2$ together represent propane-1,3-diyl(trimethylene) and $R^3$ represents $C_1$-$C_3$-alkyl or, provided that R represents alkenyl, alkynyl, alkenoxy or alkynoxy and/or $R^1$ represents alkenyl or alkynyl, or provided that $R^1$ and $R^2$ together represent propane-1,3-diyl represents hydrogen or phenyl.

The active compound combinations are well tolerated by plants, have a favorable level of toxicity to warmblooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopada, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura for example *Lepisma saccharina;* from the order of the Collembola, for example *Onychiurus armatus;*

From the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichlodectes spp. and Damalinea spp.;

from the order of the Thysanoptera, for example *Hercinothrips femoralis* and Thrips tabaci;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Phophalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo Spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Ephilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costel tra zealandica;*

From the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Cestrus spp., Hypoderma spp., Tabanus spp., Tannia spp., *Bibio hortulanus, Cscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *latrodectus mactans;* from the order of the Acarina, for example *Acarus siro,* Argas spp., Crnithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably between 0.01 and 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides a method of combating pests (in particular arthropods and especially insects or acarids) which comprises applying to said pests, or to a habitat thereof, a composition according to the present invention.

The present invention further provides crops protected from damage by pests by being grown in areas in which immediately prior to and/or during the time of the growing a composition according to the present invention was applied.

It will be seen that the usual methods of providing a harvested crop may be improved by the present invention.

PREPARATIVE EXAMPLES

Example 1

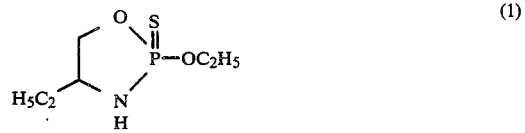

(1)

A solution of 18 g of 2-aminobutan-1-ol and 40 g of triethylamine in 100 ml of methylene chloride were added dropwise to a well-stirred solution of 36 g of O-ethyl phosphate dichloride in 300 ml of methylene chloride at 20°–25° C. in the course of 2–3 hours. The mixture was subsequently stirred overnight, washed with water and dried over sodium sulphate, the solvent was stripped off in vacuo and the residue was distilled. Yield: 26 g (66.7% of theory) 2-thioxo-2-ethoxy-4-ethyl-1,3,2-oxazaphospholane (boiling point: 88° C./0.01 mbar).

Example 2

(2)

22 g of 2-thioxo-2-chloro-3-iso-butyl-1,3,2-oxazaphospholane were initially introduced into 150 ml of toluene, and a solution of 0.1 mol of sodium ethylate in ethanol was added dropwise at an internal temperature of between 20° and 30° C. The reaction mixture was stirred for 3 hours, washed with water, dried and filtered and the filtrate was distilled. Yield: 17 g (76% of theory) 2-thioxo-2-ethoxy-3-iso-butyl-1,3,2-oxazaphospholane (boiling point: 75° C./0.01 mbar).

The following compounds of the general formula (I) could be prepared analogously to Example 1 or 2:

TABLE 1

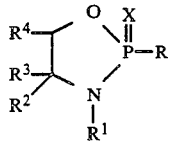
(I)

| Compound No. | R | $R^1$ | $R^2$ | $R^3$ | $R^4$ | X | Yield (% of theory) | Physical data (Refractive index; boiling point °C./mm Hg) |
|---|---|---|---|---|---|---|---|---|
| 3 | —OCH₃ | H | H | —C₃H₇—iso | H | S | 67 | |
| 4 | —OC₂H₅ | H | H | —CH₂—CH(CH₃)₂ | H | S | 65 | $n_D^{25}$: 1.5099 |
| 5 | —CH₃ | —CH₂—CH(CH₃)₂ | H | H | H | S | 76 | 78/0.01 |
| 6 | —C₆H₅ | —CH₂—CH(CH₃)₂ | H | H | H | S | 68 | 124/0.01 |
| 7 | —OCH₃ | H | H | —CH₂—CH(CH₃)₂ | H | S | 51 | $n_D^{25}$: 1.5021 |
| 8 | —OCH₃ | H | H | —CH₂—C₆H₅ | H | S | 49 | |
| 9 | —N(CH₃)₂ | —CH₂—CH(CH₃)₂ | H | H | H | S | 81 | 76/0.01 |
| 10 | —NH—C₃H₇—iso | —CH₂—CH(CH₃)₂ | H | H | H | S | 68 | 104/0.01 |
| 11 | —C₆H₅ | H | H | —C₂H₅ | H | S | 30 | 68–69 |
| 12 | —OC₂H₅ | —CH₂—CH(CH₃)₂ | H | H | H | O | 65 | 78–80/0.01 |
| 13 | —N(CH₃)₂ | —CH₂—CH(CH₃)₂ | H | H | H | O | 68 | 85/0.01 |
| 14 | —OCH₃ | —CH₂—CH(CH₃)₂ | H | H | H | S | 81 | 70/0.01 |
| 15 | —OCH₃ | H | H | —C₂H₅ | H | S | 56 | 80/0.01 |
| 16 | —CH₃ | —CH₂—CH₂—N(C₂H₅)₂ | H | H | H | S | 59 | 95/0.01 |
| 17 | —CH₃ | —C₃H₇—iso | H | H | H | S | 67 | 72/0.01 |
| 18 | —OC₃H₇—n | —CH₂—CH(CH₃)₂ | H | H | H | S | 76 | 76/0.01 |
| 19 | —OC₃H₇—iso | —CH₂—CH(CH₃)₂ | H | H | H | S | 76 | 77/0.01 |
| 20 | —CH₃ | —C₂H₅ | H | H | H | S | 55 | 62/0.01 |
| 21 | —CH₃ | H | H | —C₂H₅ | H | S | 64 | 85/0.01 |
| 22 | —NH₂ | —C₃H₇—iso | H | H | H | S | 78 | 66–67 |
| 23 | —OC₂H₅ | —CH₂—CH₂—N(C₂H₅)₂ | H | H | H | S | 38 | 112/0.01 |
| 24 | —OCH₃ | —C₃H₇—iso | H | H | H | S | 82 | 62/0.01 |
| 25 | —OC₃H₇—iso | H | H | —C₂H₅ | H | S | 43 | 91/0.01 |
| 26 | —OC₂H₅ | —C₃H₇—iso | H | H | H | S | 78 | 70/0.01 |
| 27 | —S—C₆H₅ | H | H | —C₂H₅ | H | S | 69 | |
| 28 | —SC₃H₇—n | —CH₂—CH₂—N(C₂H₅)₂ | H | H | H | S | 71 | |
| 29 | —SC₃H₇—n | H | H | —C₂H₅ | H | S | 80 | $n_D^{19}$: 1.5573 |
| 30 | —SC₃H₇—n | —C₂H₅ | H | H | H | S | 73 | $n_D^{19}$: 1.5528 |
| 31 | —N(CH₃)₂ | H | H | —C₂H₅ | H | S | 80 | $n_D^{22}$: 1.5086 |
| 32 | —OC₂H₅ | —C₂H₅ | H | H | H | S | 87 | $n_D^{22}$: 1.5028 |
| 33 | —OC₂H₅ | —C₂H₅ | H | H | H | O | 65 | 76/0.01 |
| 34 | —OC₂H₅ | —C₃H₇—iso | H | H | H | O | 71 | 79/0.01 |
| 35 | —N(CH₃)₂ | —C₃H₇—iso | H | H | H | S | 79 | 90/0.04 |
| 36 | —OC₂H₅ | H | H | —C₂H₅ | H | O | 83 | $n_D^{20}$: 1.4610 |
| 37 | —OC₂H₅ | —CH₂—CH₂—N(C₂H₅)₂ | H | H | H | O | 55 | $n_D^{20}$: 1.4679 |
| 38 | —O—C₆H₅ | —CH₂—CH₂—N(C₂H₅)₂ | H | H | H | O | 70 | $n_D^{20}$: 1.5210 |
| 39 | —O—C₆H₅ | H | H | —C₂H₅ | H | O | 68 | $n_D^{20}$: 1.5250 |
| 40 | —OCH₃ | —C₂H₅ | H | H | H | S | 74 | 63/0.01 |
| 41 | —NH—C₃H₇—iso | —C₂H₅ | H | H | H | S | 77 | 88–92/0.01 |
| 42 | —O—C₆H₄—Cl | —C₂H₅ | H | H | H | S | 68 | 120/0.01 |
| 43 | —CH₃ | H | —CH₃ | —CH₃ | H | S | 70 | $n_D^{22}$: 1.5317 |
| 44 | —OC₂H₅ | H | H | —(CH₂—CH(CH₃)₂ | H | S | 78 | 92/0.01 |

TABLE 1-continued $$\begin{array}{c} \text{R}^4\diagdown\phantom{xxx}\text{O}\phantom{xx}\text{X} \\ \phantom{xxxxx}\diagdown\phantom{xx}\|\phantom{x} \\ \text{R}^3\phantom{xxx}\text{P}\!\!\rightarrow\!\text{R} \\ \text{R}^2\phantom{xxx}\diagup \\ \phantom{xxxx}\text{N} \\ \phantom{xxxx}|\phantom{} \\ \phantom{xxxx}\text{R}^1 \end{array} \quad (I)$$

| Compound No. | R | $R^1$ | $R^2$ | $R^3$ | $R^4$ | X | Yield (% of theory) | Physical data (Refractive index; boiling point °C./mm Hg) |
|---|---|---|---|---|---|---|---|---|
| 45 | —OC$_2$H$_5$ | —CH$_3$ | —CH$_3$ | —CH$_3$ | H | S | 44 | $n_D^{22}$: 1.5062 |
| 46 | —OC$_2$H$_5$ | H | —CH$_3$ | —CH$_3$ | H | O | 73 | $n_D^{22}$: 1.4544 |
| 47 | —OC$_2$H$_5$ | H | H | —CH$_2$—CH$_2$—SCH$_3$ | H | S | 69 | $n_D^{22}$: 1.5411 |
| 48 | —CH$_3$ | H | H | —CH$_2$—CH$_2$—SCH$_3$ | H | S | 76 | $n_D^{22}$: 1.5718 |
| 49 | —OC$_2$H$_5$ | —CH$_3$ | H | H | 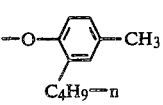 | S | 84 | $n_D^{19}$: 1.5557 |
| 50 | —OC$_2$H$_5$ | —CH$_3$ | H | —C$_3$H$_7$—iso | H | S | 45 | 74/0.01 |
| 51 | —CH$_3$ | —CH$_3$ | H | H | 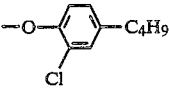 | S | 82 | $n_D^{25}$: 1.5810 |
| 52 | —OC$_3$H$_7$—n | —CH$_3$ | H | H | H | S | | 148/1.5 |
| 53 | —OC$_3$H$_7$—iso | —CH$_3$ | H | H | H | S | | 131/1.5 |
| 54 | —OC$_2$H$_5$ | H | H | H | H | S | | $n_D^{20}$: 1.5220 |
| 55 | 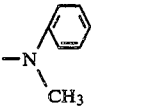 | —CH$_3$ | H | H | H | S | | $n_D^{20}$: 1.5476 |
| 56 |  | —CH$_3$ | H | H | H | S | | $n_D^{23}$: 1.5602 |
| 57 | 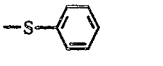 | —CH$_3$ | H | H | H | S | | $n_D^{23}$: 1.5918 |
| 58 | —OCH$_2$—CH$_2$CH(CH$_3$)$_2$ | —CH$_3$ | H | H | H | S | | $n_D^{23}$: 1.5314 |
| 59 |  | —CH$_3$ | H | H | H | S | | $n_D^{23}$: 1.5891 |
| 60 | —S—⟨phenyl⟩ | —CH$_3$ | H | H | H | S | | $n_D^{23}$: 1.6354 |
| 61 | —CH$_3$ | —CH$_3$ | H | H | H | S | | $n_D^{22}$: 1.5530 |
| 62 | —⟨phenyl⟩ | —CH$_3$ | H | H | H | S | | $n_D^{20}$: 1.6133 |
| 63 | —C$_2$H$_5$ | —CH$_3$ | H | —CH$_3$ | ⟨phenyl⟩ | S | | $n_D^{20}$: 1.5451 |
| 64 | —OC$_3$H$_7$—n | —CH$_3$ | H | —CH$_3$ | ⟨phenyl⟩ | S | | $n_D^{20}$: 1.5520 |
| 65 | —OC$_2$H$_5$ | —CH$_3$ | H | —CH$_3$ | ⟨phenyl⟩ | S | | $n_D^{20}$: 1.5495 |
| 66 | —CH$_3$ | —CH$_3$ | H | —CH$_3$ | ⟨phenyl⟩ | S | | $n_D^{20}$: 1.5613 |

TABLE 1-continued

| Compound No. | R | R¹ | R² | R³ | R⁴ | X | Yield (% of theory) | Physical data (Refractive index; boiling point °C./mm Hg) |
|---|---|---|---|---|---|---|---|---|
| 67 | —SCH₃ | —CH₃ | H | —CH₃ | 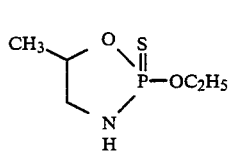 | O | | $n_D^{20}$: 1.5723 |
| 68 | 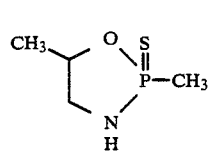 | —CH₃ | H | —CH₃ | 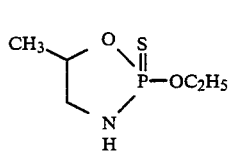 | S | | $n_D^{20}$: 1.5652 |
| 69 | —CH₃ | H | H | H | H | S | | $n_D$: 1.580 |
| 70 | —OC₂H₅ | —CH₃ | H | H | H | S | | $n_D$: 1.5040 |
| 71 | —SCH₃ | —CH₃ | H | H | H | O | | $n_D$: 1.5288 |
| 72 | —C₂H₅ | H | H | H | H | S | | $n_D$: 1.5526 |
| 73 | —SCH₃ | H | H | H | H | O | | $n_D$: 1.5475 |
| 74 | 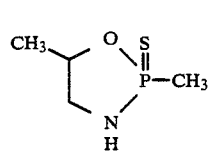 | H | H | H | H | S | | $n_D$: 1.6010 |
| 75 | —O—CH₂—CH₂—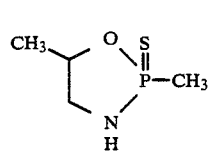 | —CH₃ | H | H | H | S | | $n_D^{23}$: 1.5795 |

Example 3

(76)

Example 4

(77)

18 g (0.1 mol) of 2-thioxo-2-chloro-5-methyl-1,3,2-oxazaphospholane were initially introduced into 100 ml of toluene, and a solution of 0.1 mol of sodium ethylate in ethanol was added dropwise at an internal temperature of between 10° and 15° C. The reaction mixture was stirred for a further two hours, washed with water, dried and filtered and the filtrate was distilled. 15 g (83% of theory) of 2-thioxo-2-ethoxy-5-methyl-1,3,2-oxazaphospholane were obtained as a colorless liquid of boiling point 78° C./0.01 mbar and of refractive index $n_D^{23}$: 1.5041.

A solution of 38 g of 1-aminopropan-2-ol and 101 g of triethylamine in 200 ml of toluene was added dropwise to a well-stirred solution of 75 g of methanethionophosphonic acid dichloride in 1,000 ml of toluene at 15°–20° C. in the course of 2–3 hours. The mixture was subsequently stirred overnight, washed with water and dried over sodium sulphate, the solvent was stripped off in vacuo and the residue was distilled. Yield: 48 g (63.5% in theory); boiling point: 74° C./0.01 mbar.

The following compounds of the general formula (Ia) were obtained analogously to Example 3 or 4:

TABLE 2

| Compound No. | R | R¹ | R² | R³ | R⁴ | X | Yield (% of theory) | Physical data melting point, boiling point °C./mbar |
|---|---|---|---|---|---|---|---|---|
| 78 | OCH₃ | H | H | H | —CH₃ | S | 78 | 64/0.01 |
| 79 | SC₃H₇—n | H | H | H | —CH₃ | S | 43 | 116/0.01 |
| 80 | OC₃H₇—n | H | H | H | —CH₃ | S | 62 | 78/0.01 |
| 81 | OC₃H₇—iso | H | H | H | —CH₃ | S | 46 | 74/0.01 |

TABLE 2-continued $$\begin{array}{c} R^4 \diagdown \overset{O}{\underset{|}{\overset{X}{\|}}} \\ R^3 \diagdown \overset{|}{\underset{|}{C}} \overset{P-R}{\underset{|}{N}} \\ R^2 \diagdown \overset{|}{\underset{R^1}{N}} \end{array}$$

| Compound No. | R | R¹ | R² | R³ | R⁴ | X | Yield (% of theory) | Physical data (Refractive index; melting point °C.; boiling point °C./mbar) |
|---|---|---|---|---|---|---|---|---|
| 82 | 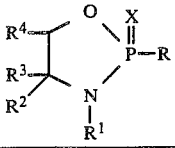 4-CH₃S-C₆H₄-O- | H | H | H | —CH₃ | S | 71 | |
| 83 |  (phenyl) | H | H | H | —CH₃ | S | 66 | 84–88 |
| 84 | —CH₂Cl | H | H | H | —CH₃ | S | 65 | 80/0.01 |
| 85 | —N(CH₃)₂ | H | H | H | —CH₃ | O | 85 | |
| 86 |  (morpholino) | H | H | H | —CH₃ | S | 54 | |
| 87 | —CH=C(CH₃)₂ | H | H | H | —CH₃ | S | 67 | |
| 88 | —OC₂H₅ | H | H | H | —CH₃ | O | 79 | $n_D^{25}$: 1.4558 |
| 89 | —SCH₃ | H | H | H | —CH₃ | O | 78 | $n_D^{25}$: 1.5215 |
| 90 | —CH₃ | C₃H₇—iso | H | H | —CH₃ | S | 41 | $n_D^{25}$: 1.5083 |
| 91 | —OCH₃ | C₃H₇—iso | H | H | —CH₃ | S | 62 | 62/0.01 |
| 92 | —N(CH₃)₂ | H | H | H | —CH₃ | S | 61 | 94/0.01 |
| 93 | 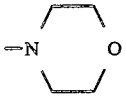 —S—C₆H₅ | H | H | H | —CH₃ | S | 61 | 48 |
| 94 | —NH—C₃H₇—iso | C₂H₅ | H | H | —C₂H₅ | S | 85 | 98/0.01 |
| 95 | —NH—C₃H₇—n | C₂H₅ | H | H | CH₃ | S | 90 | 89/0.01 |
| 96 | —OC₂H₅ | C₂H₅ | H | H | —CH₃ | S | 86 | 76/0.01 |
| 97 | 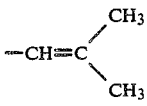 —O—C₆H₄—Cl | C₂H₅ | H | H | —CH₃ | S | 96 | |
| 98 | 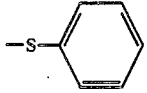 —O—C₆H₄—Cl | H | H | H | —CH₃ | S | 68 | $n_D^{21}$: 1.5318 |
| 99 |  —O—C₆H₄—Cl | C₂H₅ | H | H | —C₂H₅ | S | 69 | $n_D^{19}$: 1.5409 |
| 100 | —OCH₃ | C₂H₅ | H | H | —C₂H₅ | S | 91 | 78/0.01 |
| 101 | —OCH₃ | C₂H₅ | H | H | —CH₃ | S | 72 | 64/0.01 |
| 102 | —OC₂H₅ | C₂H₅ | H | H | —C₂H₅ | S | 85 | 69/0.01 |

TABLE 2-continued $$\begin{array}{c} R^4 \underset{R^3}{\overset{O}{\underset{R^2}{\bigg|}}} \underset{N}{\overset{X}{\underset{\|}{P}}} - R \\ \phantom{xxxx} R^1 \end{array}$$

| No. | R | R¹ | R² | R³ | R⁴ | X | Yield % | bp/mmHg or n_D |
|---|---|---|---|---|---|---|---|---|
| 103 | –O–C₆H₃(CH₃)(SCH₃) | C₂H₅ | H | H | –C₂H₅ | S | 82 | $n_D^{22}$: 1.5751 |
| 104 | –CH₃ | C₂H₅ | H | H | –CH₃ | S | 78 | 86/0.01 |
| 105 | –S–C₆H₅ | C₂H₅ | H | H | –CH₃ | S | 73 | $n_D^{19}$: 1.5992 |
| 106 | –NH₂ | C₂H₅ | H | H | –CH₃ | S | 78 | |
| 107 | –SC₃H₇–n | –C₂H₅ | H | H | –CH₃ | S | 77 | |
| 108 | –OC₂H₅ | –C₂H₅ | H | H | –CH₃ | O | 78 | 78/0.01 |
| 109 | –OC₂H₅ | –C₂H₅ | H | H | –C₂H₅ | O | 72 | 82/0.01 |
| 110 | –CH₃ | –C₂H₅ | H | H | –C₂H₅ | S | 79 | 82/0.01 |
| 111 | –CH₃ | –C₂H₅ | H | –CH₃ | –CH₃ | S | 41 | 74/0.01 |
| 112 | –N(CH₃)₂ | –C₂H₅ | H | H | –C₂H₅ | O | 63 | 89/0.01 |
| 113 | –OC₂H₅ | –C₂H₅ | H | –CH₃ | –CH₃ | O | 68 | 72/0.01 |
| 114 | –OC₂H₅ | –C₃H₇–iso | H | H | –CH₃ | O | 71 | 74/0.01 |
| 115 | –O–C₆H₅ | –C₂H₅ | H | H | –C₂H₅ | O | 90 | $n_D^{20}$: 1.5072 |
| 116 | –O–C₆H₄–Cl | –C₂H₅ | H | H | –C₂H₅ | O | 74 | $n_D^{19}$: 1.5187 |
| 117 | –CH₃ | –CH₃ | H | H | –C₂H₅ | S | 70 | 75/0.01 |
| 118 | –O–C₆H₅ | –C₃H₇–iso | H | H | –CH₃ | O | 84 | $n_D^{21}$: 1.5079 |
| 119 | –OCH₃ | –CH₃ | H | H | –C₂H₅ | S | 77 | 68/0.01 |
| 120 | –OCH₃ | –C₂H₅ | H | –CH₃ | –CH₃ | S | 72 | 82/0.01 |
| 121 | –O–C₆H₄–Cl | –C₂H₅ | H | –CH₃ | –CH₃ | S | 70 | |
| 122 | –S–C₆H₅ | –C₂H₅ | H | –CH₃ | –CH₃ | S | 91 | $n_D^{21}$: 1.5856 |
| 123 | –OC₂H₅ | –CH₃ | H | H | –C₂H₅ | S | 69 | 74/0.01 |
| 124 | –OC₂H₅ | –C₂H₅ | H | –CH₃ | –CH₃ | S | 31 | 84/0.01 |
| 125 | –O–C₆H₄–Cl | –CH₃ | H | H | –C₂H₅ | S | 89 | 123/0.01 |
| 126 | –SC₃H₇–n | –C₃H₇–iso | H | H | –CH₃ | S | 71 | 86/0.01 |

TABLE 2-continued

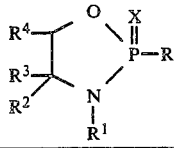

| No. | R | R¹ | R² | R³ | R⁴ | X | Yield (% of theory) | Physical data (Refractive index; melting point °C./ boiling point °C./mbar) |
|---|---|---|---|---|---|---|---|---|
| 127 | 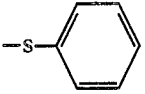 | —CH₃ | H | H | —C₂H₅ | S | 66 | 134/0.01 |
| 128 | —OC₂H₅ | —C₃H₇—iso | H | H | —CH₃ | S | 81 | 69/0.01 |

| Compound No. | R | R¹ | R² | R³ | R⁴ | X | Yield (% of theory) | Physical data (Refractive index; melting point °C./ boiling point °C./mbar) |
|---|---|---|---|---|---|---|---|---|
| 129 | 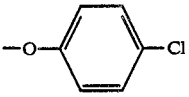 | —C₃H₇—iso | H | H | —CH₃ | S | 69 | 124/0.01 |
| 130 | —OC₂H₅ | —CH₃ | H | H | —C₂H₅ | O | 78 | 72/0.01 |
| 131 | —O—CH₂—C≡CH | —C₂H₅ | H | H | —CH₃ | S | 73 | |
| 132 | —CH₃ | —C₃H₇—n | H | H | —CH₃ | S | 83 | 75/0.01 |
| 133 | —OC₂H₅ | —C₃H₇—n | H | H | —CH₃ | S | 90 | 67/0.01 |
| 134 | —O—CH₂—CH=CH₂ | —C₂H₅ | H | H | —CH₃ | S | 73 | 80–85/0.01 |
| 135 | —O—CH₂—CH=C(CH₃)₂ | —C₂H₅ | H | H | —CH₃ | S | 29 | $n_D^{22}$: 1.5072 |
| 136 | —OC₂H₅ | —CH₂—CH₂—CH₂— | | H | H | S | 66 | 96/0.01 |
| 137 | —OC₂H₅ | —C₂H₅ | H | H | —C₂H₅ | S | 76 | 70/0.01 |
| 138 | —CH₃ | —CH₂—CH₂—CH₂— | | H | H | S | 54 | 82–84 |

| Compound No. | R | R¹ | R² | R³ | R⁴ | X | Yield (% of theory) | Physical data (Refractive index; boiling point °C./mbar) |
|---|---|---|---|---|---|---|---|---|
| 139 | —CH₃ | —C₃H₇—n | H | H | —C₂H₅ | S | 68 | 78/0.01 |
| 140 | —OC₃H₇—n | —C₃H₇—n | H | H | —C₂H₅ | S | 69 | 84/0.01 |
| 141 | —O—CH₂—CH=CH₂ | —C₃H₇—n | H | H | —C₂H₅ | S | 67 | 88/0.01 |
| 142 | —CH₃ | —CH₂—CH=CH₂ | H | H | H | S | 71 | 78/0.01 |
| 143 | —OC₂H₅ | —CH₂—CH=CH₂ | H | H | H | S | 82 | 83/0.01 |
| 144 | —O—CH₂—C≡CH | —C₃H₇—n | H | H | —C₂H₅ | S | 73 | 88/0.01 |
| 145 | —O—CH₂—C≡CH | —CH₂—CH=CH₂ | H | H | H | S | 43 | 80–85/0.01 |
| 146 | —OCH₃ | —CH₂—CH=CH₂ | H | H | H | S | 43 | 63–65/0.01 |
| 147 | —O—CH₂—CH=CH₂ | —CH₂—CH=CH₂ | H | H | H | S | 21 | 85–90/0.01 |
| 148 | —CH₃ | —CH₂—CH=CH₂ | H | H | —C₂H₅ | S | 80 | 67/0.01 |

| Compound No. | R | R¹ | R² | R³ | R⁴ | X | Yield (% of theory) | Physical data (Refractive index; melting point °C./ boiling point °C./mbar) |
|---|---|---|---|---|---|---|---|---|
| 149 | —OC₂H₅ | —CH₂—CH=CH₂ | H | H | —C₂H₅ | S | 83 | 78/0.01 |
| 150 | —OCH₃ | —CH₂—CH=CH₂ | H | H | —C₂H₅ | S | 78 | 71/0.01 |
| 151 | —O—CH₂—CH=CH₂ | —CH₂—CH=CH₂ | H | H | —C₂H₅ | S | 67 | 85/0.01 |
| 152 | —O—CH₂—CH=CH₂ | —CH₃ | H | H | H | S | 65 | $n_D^{25}$: 1.5640 |
| 153 | —O—CH₂—C≡CH | —CH₃ | H | H | H | S | 66 | 37 |
| 154 | —O—CH₂—C≡CH | —CH₂—CH=CH₂ | H | H | —C₂H₅ | S | | |
| 155 | —CH₃ | —CH₃ | H | H | —CH₃ | S | | |
| 156 | —OC₂H₅ | —CH₃ | H | H | —CH₃ | S | | |
| 157 | —OCH₃ | —CH₃ | H | H | —CH₃ | S | | |
| 158 | —OCH₂CH=CH₂ | —CH₃ | H | H | —CH₃ | S | | |
| 159 | —OCH₂—C≡CH | —CH₃ | H | H | 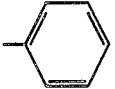 | S | | |
| 160 | —OCH₂C≡CH | —CH₃ | —CH₃ | H |  | S | | $n_D^{20}$: 1.5700 |
| 161 | —OCH₂—CH=CH₂ | —CH₃ | —CH₃ | H | 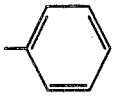 | S | | |

TABLE 2-continued

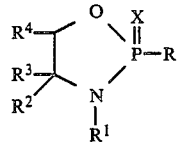

| | | R² | R³ | R⁴ | X | |
|---|---|---|---|---|---|---|
| 162 | —OCH₂—C≡CH | H | H | H | S | $n_D^{20}$: 1.5592 |

The pesticidal activity of the compositions according to the present invention is illustrated by the following biological test examples wherein the known active agents have the following formulas:

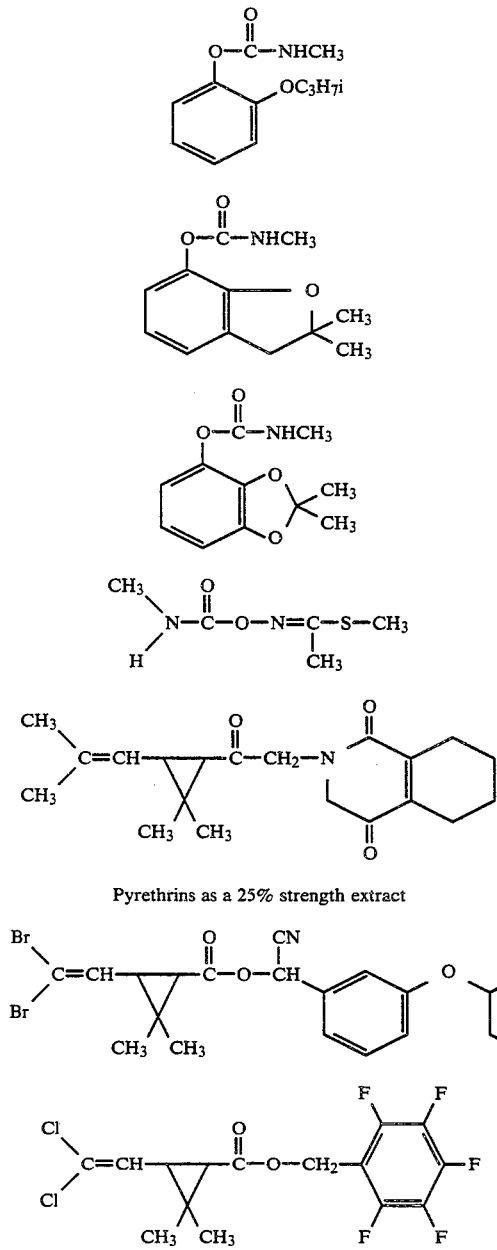

Pyrethrins as a 25% strength extract (F)

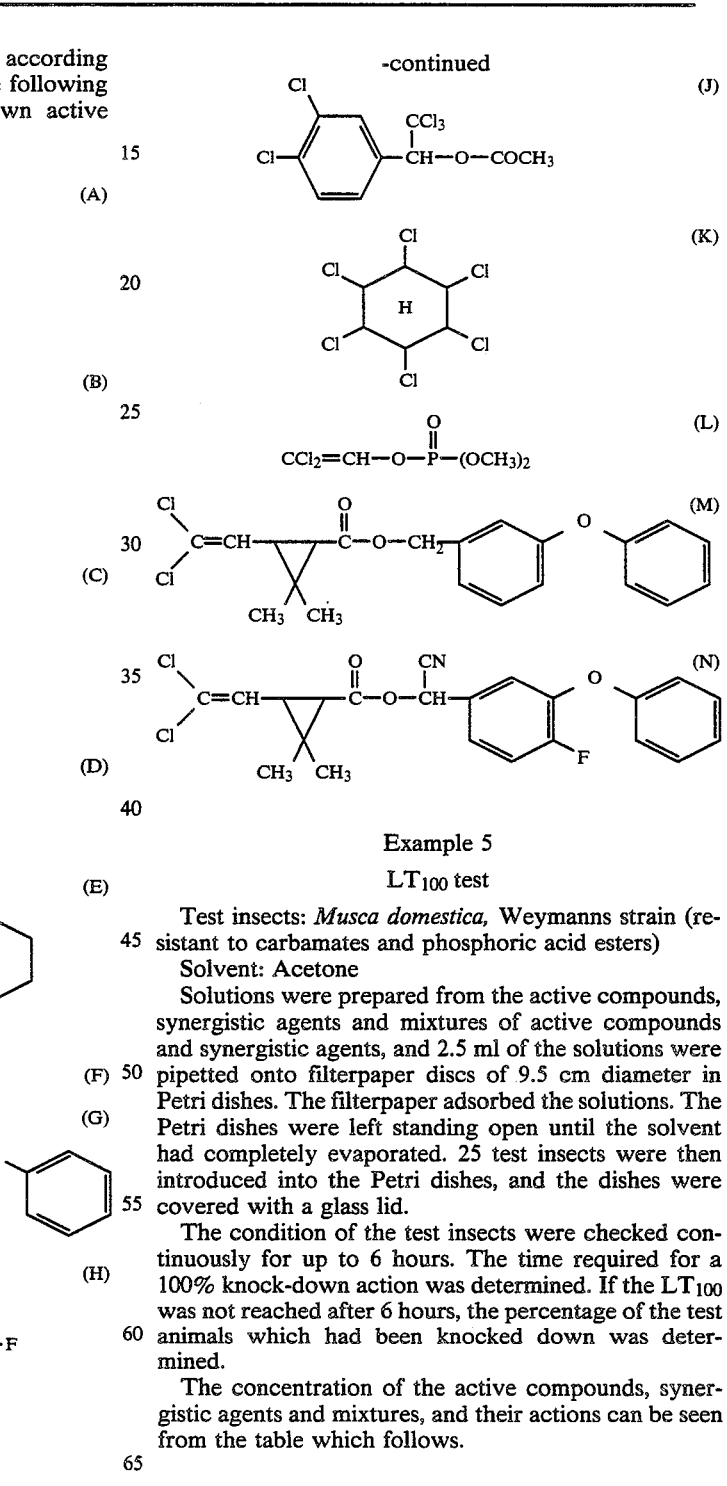

Example 5

LT₁₀₀ test

Test insects: *Musca domestica*, Weymanns strain (resistant to carbamates and phosphoric acid esters)

Solvent: Acetone

Solutions were prepared from the active compounds, synergistic agents and mixtures of active compounds and synergistic agents, and 2.5 ml of the solutions were pipetted onto filterpaper discs of 9.5 cm diameter in Petri dishes. The filterpaper adsorbed the solutions. The Petri dishes were left standing open until the solvent had completely evaporated. 25 test insects were then introduced into the Petri dishes, and the dishes were covered with a glass lid.

The condition of the test insects were checked continuously for up to 6 hours. The time required for a 100% knock-down action was determined. If the LT₁₀₀ was not reached after 6 hours, the percentage of the test animals which had been knocked down was determined.

The concentration of the active compounds, synergistic agents and mixtures, and their actions can be seen from the table which follows.

TABLE 3

LT₁₀₀ Test with the multi-resistant Weymanns strain of *Musca domestica*

| Active Compound | Synergistic Agent | Concentration % | LT₁₀₀ |
|---|---|---|---|
| A | | 1.0 | 360' = 0% |
| B | | 1.0 | 360' = 0% |
| C | | 1.0 | 360' = 0% |
| D | | 0.2 | 360' = 0% |
| E | | 0.2 | 360' = 0% |
| F | | 0.2 | 105' |
| G | | 0.008 | 75' |
| H | | 0.0016 | 45' |
| J | | 1.0 | 360' = 40% |
| K | | 0.04 | 360' = 95% |
| L | | 0.008 | 360' = 70% |
| | 9 | 1.0 | 360' = 70% |
| | 2 | 1.0 | 360' = 65% |
| | 19 | 1.0 | 360' = 5% |
| | 22 | 1.0 | 360' = 0% |
| | 1 | 1.0 | 150' |
| | 25 | 1.0 | 360' = 50% |
| | 26 | 1.0 | 360' = 85% |
| | 24 | 1.0 | 360' = 90% |
| | 29 | 1.0 | 360' = 0% |
| | 30 | 1.0 | 360' = 0% |
| | 31 | 0.2 | 360' = 70% |
| | 32 | 0.2 | 360' = 0% |
| | 35 | 1.0 | 360' = 60% |
| | 16 | 1.0 | 360' = 0% |
| | 17 | 0.2 | 360' = 70% |
| | 20 | 1.0 | 360' = 20% |
| | 21 | 1.0 | 360' = 5% |
| | 40 | 0.2 | 360' = 0% |
| | 41 | 0.2 | 360' = 0% |
| | 43 | 1.0 | 360' = 30% |
| | 44 | 0.2 | 360' |
| | 46 | 1.0 | 360' = 65% |
| | 55 | 1.0 | 360' = 70% |
| | 52 | 1.0 | 360' = 15% |
| | 53 | 1.0 | 360' = 25% |
| A+ | piperonyl butoxide | 0.2 + 0.2 | 360' = 90% |
| A+ | 9 | 0.04 + 0.04 | 180' |
| A+ | 2 | 0.04 + 0.04 | 150' |
| A+ | 19 | 0.04 + 0.04 | 180' |
| A+ | 22 | 0.04 + 0.04 | 180' |
| A+ | 1 | 0.04 + 0.04 | 75' |
| A+ | 25 | 0.04 + 0.04 | 105' |
| A+ | 26 | 0.04 + 0.04 | 150' |
| A+ | 24 | 0.2 + 0.2 | 75' |
| A+ | 27 | 0.2 + 0.2 | 360' |
| A+ | 30 | 0.2 + 0.2 | 240' |
| A+ | 31 | 0.2 + 0.2 | 120' |
| A+ | 32 | 0.2 + 0.2 | 150' |
| A+ | 35 | 0.04 + 0.04 | 180' |
| A+ | 16 | 0.2 + 0.2 | 240' |
| A+ | 17 | 0.04 + 0.04 | 90' |
| A+ | 20 | 0.04 + 0.04 | 150' |
| A+ | 21 | 0.2 + 0.2 | 150' |
| A+ | 40 | 0.04 + 0.04 | 150' |
| A+ | 41 | 0.2 + 0.2 | 150' |
| A+ | 43 | 0.04 + 0.04 | 240' |
| A+ | 44 | 0.04 + 0.04 | 120' |
| A+ | 46 | 0.04 + 0.04 | 105' |
| A+ | 55 | 0.2 + 0.2 | 240' |
| A+ | 52 | 0.2 + 0.2 | 210' |
| A+ | 53 | 0.2 + 0.2 | 360' |
| B+ | Piperonyl butoxide | 0.04 + 0.04 | 180' |
| B+ | 9 | 0.04 + 0.04 | 105' |
| B+ | 46 | 0.04 + 0.04 | 120' |
| B+ | 17 | 0.04 + 0.04 | 90' |
| B+ | 2 | 0.04 + 0.04 | 120' |
| B+ | 1 | 0.04 + 0.04 | 90' |
| B+ | 25 | 0.04 + 0.04 | 120' |
| B+ | 31 | 0.04 + 0.04 | 150' |
| B+ | 32 | 0.04 + 0.04 | 105' |
| B+ | 35 | 0.04 + 0.04 | 105' |
| B+ | 40 | 0.04 + 0.04 | 105' |
| B+ | 44 | 0.04 + 0.04 | 90' |
| C+ | Piperonyl butoxide | 0.2 + 0.2 | 360' = 85% |
| C+ | 9 | 0.04 + 0.04 | 180' |
| C+ | 46 | 0.04 + 0.04 | 150' |
| C+ | 17 | 0.04 + 0.04 | 120' |
| C+ | 2 | 0.2 + 0.2 | 150' |
| C+ | 20 | 0.2 + 0.2 | 105' |
| C+ | 1 | 0.04 + 0.04 | 150' |
| C+ | 25 | 0.04 + 0.04 | 210' |
| C+ | 26 | 0.2 + 0.2 | 150' |
| C+ | 31 | 0.2 + 0.2 | 180' |
| C+ | 32 | 0.2 + 0.2 | 150' |
| C+ | 35 | 0.04 + 0.04 | 210' |
| C+ | 40 | 0.04 + 0.04 | 180' |
| C+ | 44 | 0.04 + 0.04 | 210' |
| D+ | Piperonyl butoxide | 0.2 + 0.2 | 240' |
| D+ | 9 | 0.04 + 0.04 | 180' |
| D+ | 46 | 0.04 + 0.04 | 150' |
| D+ | 17 | 0.04 + 0.04 | 105' |
| D+ | 2 | 0.04 + 0.04 | 150' |
| D+ | 20 | 0.2 + 0.2 | 105' |
| D+ | 1 | 0.04 + 0.04 | 150' |
| D+ | 25 | 0.04 + 0.04 | 150' |
| D+ | 26 | 0.04 + 0.04 | 150' |
| D+ | 31 | 0.04 + 0.04 | 210' |
| D+ | 32 | 0.2 + 0.2 | 90' |
| D+ | 35 | 0.04 + 0.04 | 180' |
| D+ | 40 | 0.2 + 0.2 | 60' |
| D+ | 44 | 0.2 + 0.2 | 75' |
| E+ | Piperonyl butoxide | 0.2 + 0.2 | 45' |
| E+ | 1 | 0.2 + 0.2 | 30' |
| F+ | Piperonyl butoxide | 0.2 + 0.2 | 60' |
| F+ | 9 | 0.2 + 0.2 | 45' |
| F+ | 46 | 0.2 + 0.2 | 45' |
| F+ | 17 | 0.2 + 0.2 | 30' |
| F+ | 1 | 0.2 + 0.2 | 45' |
| F+ | 32 | 0.2 + 0.2 | 45' |
| F+ | 35 | 0.2 + 0.2 | 30' |
| F+ | 40 | 0.2 + 0.2 | 30' |
| F+ | 44 | 0.2 + 0.2 | 45' |
| G+ | Piperonyl butoxide | 0.008 + 0.008 | 75' |
| G+ | 9 | 0.008 + 0.008 | 60' |
| G+ | 1 | 0.008 + 0.008 | 60' |
| G+ | 26 | 0.008 + 0.008 | 60' |
| G+ | 32 | 0.008 + 0.008 | 60' |
| G+ | 40 | 0.008 + 0.008 | 60' |
| G+ | 44 | 0.008 + 0.008 | 60' |
| H+ | Piperonyl butoxide | 0.0016 + 0.0016 | 45' |
| H+ | 31 | 0.0016 + 0.0016 | 30' |
| J+ | Piperonyl butoxide | 1.0 + 1.0 | 360' = 75% |
| J+ | 9 | 0.04 + 0.04 | 360' |
| J+ | 22 | 0.04 + 0.04 | 360' = 95% |
| J+ | 1 | 0.04 + 0.04 | 180' |
| J+ | 25 | 0.04 + 0.04 | 360' |
| J+ | 26 | 0.04 + 0.04 | 360' |
| J+ | 24 | 0.04 + 0.04 | 360' |
| J+ | 29 | 1.0 + 1.0 | 240' |
| J+ | 31 | 0.04 + 0.04 | 360' |
| J+ | 32 | 1.0 + 1.0 | 180' |
| J+ | 35 | 0.04 + 0.04 | 240' |
| J+ | 17 | 0.04 + 0.04 | 180' |
| J+ | 20 | 1.0 + 1.0 | 90' |
| J+ | 40 | 0.04 + 0.04 | 210' |
| J+ | 41 | 0.04 + 0.04 | 360' |
| J+ | 43 | 1.0 + 1.0 | 105' |
| J+ | 44 | 0.04 + 0.04 | 180' |
| J+ | 46 | 0.04 + 0.04 | 360' |
| K+ | Piperonyl butoxide | 0.04 + 0.04 | 360' |
| K+ | 46 | 0.008 + 0.008 | 180' |
| K+ | 17 | 0.008 + 0.008 | 180' |
| K+ | 2 | 0.04 + 0.04 | 210' |

TABLE 3-continued

LT$_{100}$ Test with the multi-resistant Weymanns strain of *Musca domestica*

| Active Compound | Synergistic Agent | Concentration % | LT$_{100}$ |
|---|---|---|---|
| K+ | 20 | 0.008 + 0.008 | 180' |
| K+ | 1 | 0.008 + 0.008 | 210' |
| K+ | 25 | 0.04 + 0.04 | 180' |
| K+ | 26 | 0.04 + 0.04 | 210' |
| K+ | 32 | 0.04 + 0.04 | 210' |
| K+ | 40 | 0.04 + 0.04 | 120' |
| K+ | 44 | 0.008 + 0.008 | 210' |
| L+ | Piperonyl butoxide | 0.008 + 0.008 | 360' |
| L+ | 46 | 0.008 + 0.008 | 150' |
| L+ | 17 | 0.008 + 0.008 | 105' |
| L+ | 2 | 0.008 + 0.008 | 150' |
| L+ | 1 | 0.008 + 0.008 | 150' |
| L+ | 25 | 0.008 + 0.008 | 150' |
| L+ | 26 | 0.008 + 0.008 | 150' |
| L+ | 35 | 0.008 + 0.008 | 180' |
| L+ | 40 | 0.008 + 0.008 | 180' |
| L+ | 44 | 0.008 + 0.008 | 120' |

Example 6

The test of Example 5 is repeated with a different population of the same insects and the following results were obtained:

TABLE 4

LT$_{100}$ Test with the multi-resistant Weymanns strain of *Musca Domestica*

| Active Compound | Synergistic Agent | Concentration % | LT$_{100}$ |
|---|---|---|---|
| A |  | 1.0 | 360' = 0% |
| B |  | 1.0 | 360' = 0% |
| C |  | 1.0 | 360' = 0% |
| D |  | 0.04 | 360' = 0% |
| E |  | 0.04 | 360' = 45% |
| G |  | 0.008 | 75' |
| H |  | 0.0016 | 45' |
| J |  | 1.0 | 360' = 60% |
| K |  | 1.0 | 360' = 40% |
| M |  | 0.0016 | 360' = 5% |
|  | (76) | 1.0 | 360' = 5% |
|  | (77) | 0.2 | 360' = 10% |
|  | (81) | 1.0 | 360' = 5% |
|  | (102) | 0.2 | 360' = 15% |
|  | (106) | 0.2 | 360' = 70% |
|  | (94) | 1.0 | 360' = 5% |
|  | (95) | 1.0 | 360' = 5% |
|  | (96) | 0.2 | 360' = 25% |
|  | (97) | 1.0 | 360' = 5% |
|  | (100) | 0.2 | 360' = 25% |
|  | (80) | 1.0 | 360' = 0% |
|  | (87) | 1.0 | 360' = 0% |
|  | (84) | 1.0 | 360' = 0% |
|  | (91) | 1.0 | 360' = 0% |
|  | (92) | 1.0 | 360' = 0% |
|  | (110) | 0.2 | 360' = 50% |
|  | (111) | 0.2 | 360' = 30% |
|  | (112) | 0.2 | 360' = 0% |
|  | (128) | 1.0 | 360' = 0% |
|  | (129) | 1.0 | 360' = 0% |
|  | (132) | 1.0 | 360' = 90% |
|  | (134) | 1.0 | 360' = 25% |
|  | (104) | 0.2 | 360' = 0% |
|  | (119) | 0.2 | 360' = 70% |
|  | (123) | 0.2 | 360' = 50% |
|  | (126) | 1.0 | 360' = 15% |
|  | (120) | 1.0 | 360' = 90% |
|  | (121) | 1.0 | 360' = 10% |
|  | (117) | 0.2 | 360' = 0% |
|  | (101) | 0.2 | 360' = 70% |
|  | (131) | 1.0 | 360' = 0% |
|  | (144) | 1.0 | 360' = 20% |
|  | (141) | 1.0 | 360' = 0% |
|  | (142) | 0.2 | 360' = 95% |
|  | (145) | 1.0 | 360' = 0% |
|  | (146) | 0.2 | 360' = 20% |
|  | (149) | 0.2 | 360' = 20% |
|  | (148) | 1.0 | 360' = 90% |
|  | (147) | 0.2 | 360' = 0% |
|  | (152) | 1.0 | 360' = 20% |
|  | (153) | 1.0 | 360' = 80% |
| A+ | Piperonyl butoxide | 0.2 + 0.2 | 360' = 85% |
| A+ | 76 | 0.04 + 0.04 | 240' |
| A+ | 77 | 0.04 + 0.04 | 150' |
| A+ | 81 | 0.04 + 0.04 | 360' |
| A+ | 84 | 0.04 + 0.04 | 120' |
| A+ | 80 | 0.04 + 0.04 | 180' |
| A+ | 87 | 0.2 + 0.2 | 180' |
| A+ | 96 | 0.04 + 0.04 | 150' |
| A+ | 97 | 0.2 + 0.2 | 150' |
| A+ | 100 | 0.04 + 0.04 | 150' |
| A+ | 91 | 0.04 + 0.04 | 150' |
| A+ | 92 | 0.04 + 0.04 | 210' |
| A+ | 94 | 0.04 + 0.04 | 360' = 95% |
| A+ | 95 | 0.04 + 0.04 | 210' |
| A+ | 106 | 0.04 + 0.04 | 240' |
| A+ | 102 | 0.2 + 0.2 | 90' |
| A+ | 110 | 0.04 + 0.04 | 90' |
| A+ | 111 | 0.04 + 0.04 | 150' |
| A+ | 107 | 0.2 + 0.2 | 210' |
| A+ | 128 | 0.04 + 0.04 | 150' |
| A+ | 132 | 0.04 + 0.04 | 105' |
| A+ | 134 | 0.04 + 0.04 | 150' |
| A+ | 104 | 0.04 + 0.04 | 90' |
| A+ | 123 | 0.04 + 0.04 | 75' |
| A+ | 126 | 0.2 + 0.2 | 240' |
| A+ | 117 | 0.04 + 0.04 | 150' |
| A+ | 119 | 0.04 + 0.04 | 90' |
| A+ | 120 | 0.008 + 0.008 | 360' |
| A+ | 101 | 0.04 + 0.04 | 105' |
| A+ | 131 | 0.04 + 0.04 | 90' |
| A+ | 144 | 0.04 + 0.04 | 150' |
| A+ | 141 | 0.04 + 0.04 | 210' |
| A+ | 145 | 0.04 + 0.04 | 180' |
| A+ | 146 | 0.04 + 0.04 | 210' |
| A+ | 149 | 0.04 + 0.04 | 90' |
| A+ | 148 | 0.04 + 0.04 | 75' |
| A+ | 147 | 0.04 + 0.04 | 180' |
| A+ | 152 | 0.04 + 0.04 | 180' |
| A+ | 153 | 0.04 + 0.04 | 180' |
| B+ | Piperonyl butoxide | 0.2 + 0.2 | 360' = 70% |
| B+ | 80 | 0.2 + 0.2 | 90' |
| B+ | 84 | 0.2 + 0.2 | 90' |
| B+ | 92 | 0.2 + 0.2 | 120' |
| B+ | 95 | 0.2 + 0.2 | 150' |
| B+ | 101 | 0.04 + 0.04 | 120' |
| B+ | 104 | 0.04 + 0.04 | 105' |
| B+ | 110 | 0.04 + 0.04 | 180' |
| B+ | 120 | 0.04 + 0.04 | 105' |
| B+ | 131 | 0.04 + 0.04 | 90' |
| B+ | 132 | 0.04 + 0.04 | 90' |
| B+ | 134 | 0.2 + 0.2 | 90' |
| B+ | 141 | 0.04 + 0.04 | 150' |
| B+ | 142 | 0.04 + 0.04 | 105' |
| B+ | 145 | 0.04 + 0.04 | 120' |
| B+ | 147 | 0.04 + 0.04 | 180' |
| C+ | Piperonyl butoxide | 1.0 + 1.0 | 360' = 25% |
| C+ | 80 | 0.04 + 0.04 | 210' |
| C+ | 84 | 0.2 + 0.2 | 210' |
| C+ | 92 | 0.2 + 0.2 | 210' |
| C+ | 95 | 0.2 + 0.2 | 180' |
| C+ | 101 | 0.04 + 0.04 | 180' |
| C+ | 104 | 0.2 + 0.2 | 150' |
| C+ | 111 | 0.2 + 0.2 | 150' |
| C+ | 120 | 0.04 + 0.04 | 210' |
| C+ | 131 | 0 04 + 0.04 | 180' |
| C+ | 132 | 0.04 + 0.04 | 150' |
| C+ | 134 | 0.2 + 0.2 | 150' |

TABLE 4-continued

LT$_{100}$ Test with the multi-resistant Weymanns strain of *Musca Domestica*

| Active Compound | Synergistic Agent | Concentration % | LT$_{100}$ | |
|---|---|---|---|---|
| C+ | 141 | 0.04 + 0.04 | 180' | |
| C+ | 142 | 0.2 + 0.2 | 120' | |
| C+ | 145 | 0.2 + 0.2 | 180' | |
| C+ | 147 | 0.2 + 0.2 | 150' | |
| C+ | Piperonyl butoxide | 0.04 + 0.04 | 210' | |
| D+ | 76 | 0.04 + 0.04 | 180' | |
| D+ | 77 | 0.04 + 0.04 | 120' | |
| D+ | 80 | 0.04 + 0.04 | 90' | |
| D+ | 84 | 0.04 + 0.04 | 120' | |
| D+ | 92 | 0.04 + 0.04 | 90' | |
| D+ | 95 | 0.04 + 0.04 | 120' | |
| D+ | 101 | 0.008 + 0.008 | 150' | |
| D+ | 104 | 0.04 + 0.04 | 105' | |
| D+ | 110 | 0.04 + 0.04 | 105' | |
| D+ | 111 | 0.04 + 0.04 | 120' | |
| D+ | 120 | 0.04 + 0.04 | 90' | |
| D+ | 131 | 0.04 + 0.04 | 90' | |
| D+ | 132 | 0.04 + 0.04 | 75' | |
| D+ | 134 | 0.04 + 0.04 | 105' | |
| D+ | 141 | 0.04 + 0.04 | 120' | |
| D+ | 142 | 0.04 + 0.04 | 90' | |
| D+ | 145 | 0.04 + 0.04 | 90' | |
| D+ | 147 | 0.04 + 0.04 | 90' | |
| E+ | Piperonyl butoxide | 0.04 + 0.04 | 150' | |
| E+ | 80 | 0.04 + 0.04 | 75' | |
| E+ | 87 | 0.008 + 0.008 | 60' | |
| E+ | 92 | 0.04 + 0.04 | 75' | |
| E+ | 101 | 0.04 + 0.04 | 90' | |
| E+ | 104 | 0.04 + 0.04 | 120' | |
| E+ | 131 | 0.04 + 0.04 | 60' | |
| E+ | 132 | 0.04 + 0.04 | 45' | |
| E+ | 134 | 0.04 + 0.04 | 75' | |
| E+ | 141 | 0.04 + 0.04 | 45' | |
| E+ | 142 | 0.04 + 0.04 | 45' | |
| E+ | 145 | 0.04 + 0.04 | 105' | |
| E+ | 147 | 0.04 + 0.04 | 60' | |
| N+ | Piperonyl butoxide | 0.0016 + 0.0016 | 180' | |
| N+ | 80 | 0.0016 + 0.0016 | 90' | |
| N+ | 134 | 0.0016 + 0.0016 | 150' | |
| H+ | Piperonyl butoxide | 0.0016 + 0.0016 | 90' | |
| H+ | 76 | 0.0016 + 0.0016 | 45' | |
| H+ | 81 | 0.0016 + 0.0016 | 45' | |
| H+ | 84 | 0.0016 + 0.0016 | 45' | |
| H+ | 101 | 0.0016 + 0.0016 | 45' | |
| H+ | 104 | 0.0016 + 0.0016 | 60' | |
| H+ | 120 | 0.0016 + 0.0016 | 60' | |
| H+ | 134 | 0.0016 + 0.0016 | 60' | |
| H+ | 142 | 0.0016 + 0.0016 | 60' | |
| H+ | 147 | 0.0016 + 0.0016 | 60' | |
| J+ | Piperonyl butoxide | 0.2 + 0.2 | 360' | = 80% |
| J+ | 76 | 0.04 + 0.04 | 360' | |
| J+ | 77 | 0.04 + 0.04 | 210' | |
| J+ | 80 | 0.04 + 0.04 | 360' | = 90% |
| J+ | 96 | 0.04 + 0.04 | 360' | = 95% |
| J+ | 100 | 0.04 + 0.04 | 360' | |
| J+ | 91 | 0.04 + 0.04 | 240' | |
| J+ | 92 | 0.04 + 0.04 | 360' | |
| J+ | 95 | 0.04 + 0.04 | 360' | |
| J+ | 106 | 0.04 + 0.04 | 240' | |
| J+ | 102 | 0.04 + 0.04 | 360' | = 95% |
| J+ | 81 | 0.04 + 0.04 | 360' | |
| J+ | 107 | 0.04 + 0.04 | 360' | |
| J+ | 110 | 0.04 + 0.04 | 240' | |
| J+ | 111 | 0.04 + 0.04 | 360' | |
| J+ | 128 | 0.04 + 0.04 | 360' | = 95% |
| J+ | 129 | 0.04 + 0.04 | 360' | = 80% |
| J+ | 132 | 0.04 + 0.04 | 360' | |
| J+ | 134 | 0.04 + 0.04 | 360' | = 85% |
| J+ | 104 | 0.04 + 0.04 | 360' | = 95% |
| J+ | 119 | 0.04 + 0.04 | 360' | |
| J+ | 123 | 0.04 + 0.04 | 360' | = 90% |
| J+ | 126 | 0.04 + 0.04 | 360' | = 85% |
| J+ | 120 | 0.04 + 0.04 | 360' | |
| J+ | 121 | 0.04 + 0.04 | 360' | = 80% |
| J+ | 101 | 0.04 + 0.04 | 360' | |
| J+ | 131 | 0.04 + 0.04 | 210' | |
| J+ | 144 | 0.04 + 0.04 | 210' | |
| J+ | 141 | 0.04 + 0.04 | 360' | |
| J+ | 145 | 0.04 + 0.04 | 240' | |
| J+ | 146 | 0.04 + 0.04 | 180' | |
| J+ | 149 | 0.04 + 0.04 | 360' | |
| J+ | 148 | 0.04 + 0.04 | 180' | |
| J+ | 147 | 0.04 + 0.04 | 360' | = 90% |
| J+ | 151 | 0.04 + 0.04 | 360' | |
| J+ | 152 | 0.04 + 0.04 | 360' | |
| K+ | Piperonyl butoxide | 1.0 + 1.0 | 180' | |
| K+ | 92 | 0.2 + 0.2 | 120' | |
| K+ | 95 | 0.04 + 0.04 | 120' | |
| K+ | 101 | 0.2 + 0.2 | 150' | |
| K+ | 120 | 0.04 + 0.04 | 150' | |
| K+ | 131 | 0.04 + 0.04 | 150' | |
| K+ | 132 | 0.04 + 0.04 | 90' | |
| K+ | 134 | 0.2 + 0.2 | 150' | |
| K+ | 141 | 0.2 + 0.2 | 120' | |
| K+ | 142 | 0.2 + 0.2 | 90' | |
| K+ | 145 | 0.2 + 0.2 | 105' | |
| M+ | Piperonyl butoxide | 0.0016 + 0.0016 | 360' | = 10% |
| M | 92 | 0.0016 + 0.0016 | 360' | = 95% |

It will be appreciated that the instant specification and examples are set forth by way of illustration and not limitation, and that various modifications and changes may be made without departing from the spirit and scope of the present invention.

We claim:

1. 2-Ethyl-2-thiono-1,3,2-oxazaphospholane of the formula

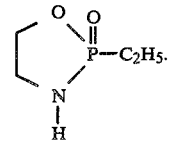

2. In a synergistic insecticidal and acaricidal composition comprising (1) an insecticidally and acaricidally active compound and (2) a synergizing agent in amount sufficient to synergize the insecticidal and acaricidal activity of the insecticidally and acaricidally active compound, the improvement which comprises employing as the synergizing agent the compound according to claim 1.

3. A method of combating pests comprising applying to the pests or a habitat thereof a pesticidally effective amount of a composition according to claim 2.

4. A composition according to claim 2, wherein (1) is selected from (A) carbamic acid esters, (B) carboxylic acid esters, including the naturally occurring and the synthetic pyrethroids, (C) phosphoric acid esters and phosphonic acid esters and (D) halogeno(cyclo)alkanes.

5. A composition according to claim 2, wherein (1) is selected from
(A) carbamic acid esters of the formula

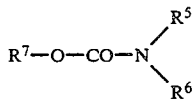

in which
R[5] represents hydrogen or $C_1$–$C_4$-alkyl,
R[6] represents $C_1$–$C_4$-alkyl, $C_1$–$C_4$-alkylcarbonyl which is optionally substituted by halogen, by hydroxyl or by methylthio, or the radical S-Z,
Z represents optionally halogen-substituted $C_1$–$C_4$-alkyl, phenyl which optionally carries one or more substituents selected from halogen, cyano, $C_1$–$C_4$-alkyl, trihalogenomethylthio, trihalogenomethyl and nitro, or $C_1$–$C_4$-alkoxycarbonyl and
R[7] represents an optionally substituted aryl, heterocyclic or oxime radical, (B) carboxylic acid esters of the formula

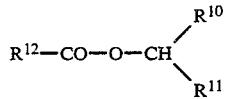

in which
R[12] represents an open-chain or cyclic alkyl radical which is optionally substituted by halogen, by alkyl, by cycloalkyl, by alkenyl which is optionally substituted by halogen and/or alkoxy, by phenyl or styryl, in either case optionally substituted by halogen or one or more substituents selected from optionally halogen-substituted alkyl, alkoxy, alkylenedioxy and alkylthio radicals, or by cycloalk(en)yl which is linked in a spirocyclic-like manner and is optionalldy halogen-substituted and optionally benzo-fused,
R[10] represents hydrogen, alkyl, halogenoalkyl, alkenyl, alkynyl or cyano and
R[11] represents an optionally substituted aryl radical or a heterocyclic radical, or
R[10] and R[11], together with the carbon atom to which the two radicals are bonded, form a cyclopentenone ring,
and naturally occurring pyrethroids, (C) phosphoric acid esters and phosphonic acid esters of the formula

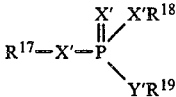

in which
X' represents oxygen or sulphur,
Y' represents oxygen, sulphur, imino or a direct bond between the P atom and R[19],
R[17] and R[18] are identical or different and each represents an optionally substituted alkyl or aryl radical and
R[19] represents an optionally substituted alkyl, aryl, heteroaryl, aralkyl or alkenyl radical, an optionally substituted oxime radical, or a radical identical to that to which it is bonded, and (D) hexachlorocyclohexane, 1,1,1-trichloro-2,2-bis-(4-chlorophenyl)-ethane, 1,1,1-trichloro-2,2,-bis-(4-methoxyphenyl)-ethane and 1,1-dichloro-2,2-bis-(4-ethylphenyl)-ethane.

* * * * *

UNITED STATES PATENT AND TRADEMARK OFFICE
CERTIFICATE OF CORRECTION

PATENT NO. : 4,609,646  
DATED : September 2, 1986  
INVENTOR(S) : Hellmut Hoffmann, et al.

Page 1 of 2

It is certified that error appears in the above-identified patent and that said Letters Patent are hereby corrected as shown below:

| | |
|---|---|
| Abstract, line 14 | After "N-" delete "alky" and substitute --alkyl-- |
| Col. 7, line 36 | Before "in which" delete "10" |
| Col. 9, line 38 | Delete "From" and substitute --from-- |
| Col. 9, line 51 | Correct spelling of --Trichodectes-- |
| Col. 9, line 62 | Correct spelling of --Phopalosiphum-- |
| Col. 10, line 43 | Delete "latrodectus" and substitute --Latrodectus-- |
| Col. 10, line 45 | Correct spelling of --Ornithodoros-- |
| Col. 14, line 26 under last column | Delete "$n_D^{22}$: 1.5028" and substitute --$n_D^{21}$: 1.5028-- |
| Col. 16, line 11 under last column | Delete "$n_D^{20}$: 1.5476" and substitute --$n_D^{23}$: 1.5476-- |
| Col. 18, line 50 | Delete "in" and substitute --of-- |
| Col. 26, line 62 | Delete "concentration" and substitute --concentrations-- |

UNITED STATES PATENT AND TRADEMARK OFFICE
CERTIFICATE OF CORRECTION

PATENT NO. : 4,609,646

DATED : September 2, 1986

INVENTOR(S) : Hellmut Hoffmann, et al.

It is certified that error appears in the above-identified patent and that said Letters Patent are hereby corrected as shown below:

Col. 32, line 41   Delete "$\overset{O}{\underset{P}{\|}}$" in formula and substitute --$\overset{S}{\underset{P}{\|}}$--

Col. 34, line 2   Correct spelling of "optionally"

Signed and Sealed this

Eighteenth Day of November, 1986

Attest:

DONALD J. QUIGG

Attesting Officer       Commissioner of Patents and Trademarks